United States Patent [19]

Whitlock et al.

[11] Patent Number: 4,821,302
[45] Date of Patent: Apr. 11, 1989

[54] METHOD AND APPARATUS FOR TRANSIENT UNIT CELL MEASUREMENT

[75] Inventors: Robert R. Whitlock, Bethesda, Md.; Justin S. Wark, Rochester, N.Y.; Allan Hauer, Los Alamos, N. Mex.

[73] Assignee: The United States of America as represented by the Secretary of the Navy, Washington, D.C.

[21] Appl. No.: 161,935

[22] Filed: Feb. 29, 1988

[51] Int. Cl.$^4$ ............................................. G01N 23/20
[52] U.S. Cl. ........................................ 378/73; 378/72; 378/87
[58] Field of Search ....................... 378/73, 72, 71, 86, 378/87

[56]         References Cited
        U.S. PATENT DOCUMENTS
    3,861,199  1/1975  Barkhoudarian ..................... 378/87

Primary Examiner—Janice A. Howell
Assistant Examiner—David P. Porta
Attorney, Agent, or Firm—Thomas E. McDonnell; George Jameson

[57]             ABSTRACT

A method and apparatus is disclosed for measuring the lattice parameters of a single crystal material while that material is undergoing a transient shock wave. In a first embodiment, a first target is located at a preselected position in space with respect to a single crystal to be measured. A first laser beam pulse is transmitted through a beam block to the crystal to produce a transient shock wave in part of the crystal. A second laser beam pulse, synchronized to the first laser beam pulse, is transmitted to the first target to cause the first target to produce first and second sets of x-rays which are Bragg-diffracted from shocked and unshocked atomic planes of the crystal as the crystal is undergoing the shock wave. A first x-ray detector records the positions of the first and second sets of Bragg-diffracted x-rays to provide a first measurement of the lattice parameters of the crystal. In a second embodiment, a third laser beam pulse, synchronized to the second laser beam pulse, is transmitted to a second target to cause the second target to produce third and fourth sets of x-rays which are Bragg-diffracted from shocked and unshocked atomic planes of the crystal as the crystal is undergoing the shocke wave. A second x-ray detector records the positions of the third and fourth sets of Bragg-diffracted x-rays to provide a second measurement of the lattice parameters of the crystal.

20 Claims, 3 Drawing Sheets

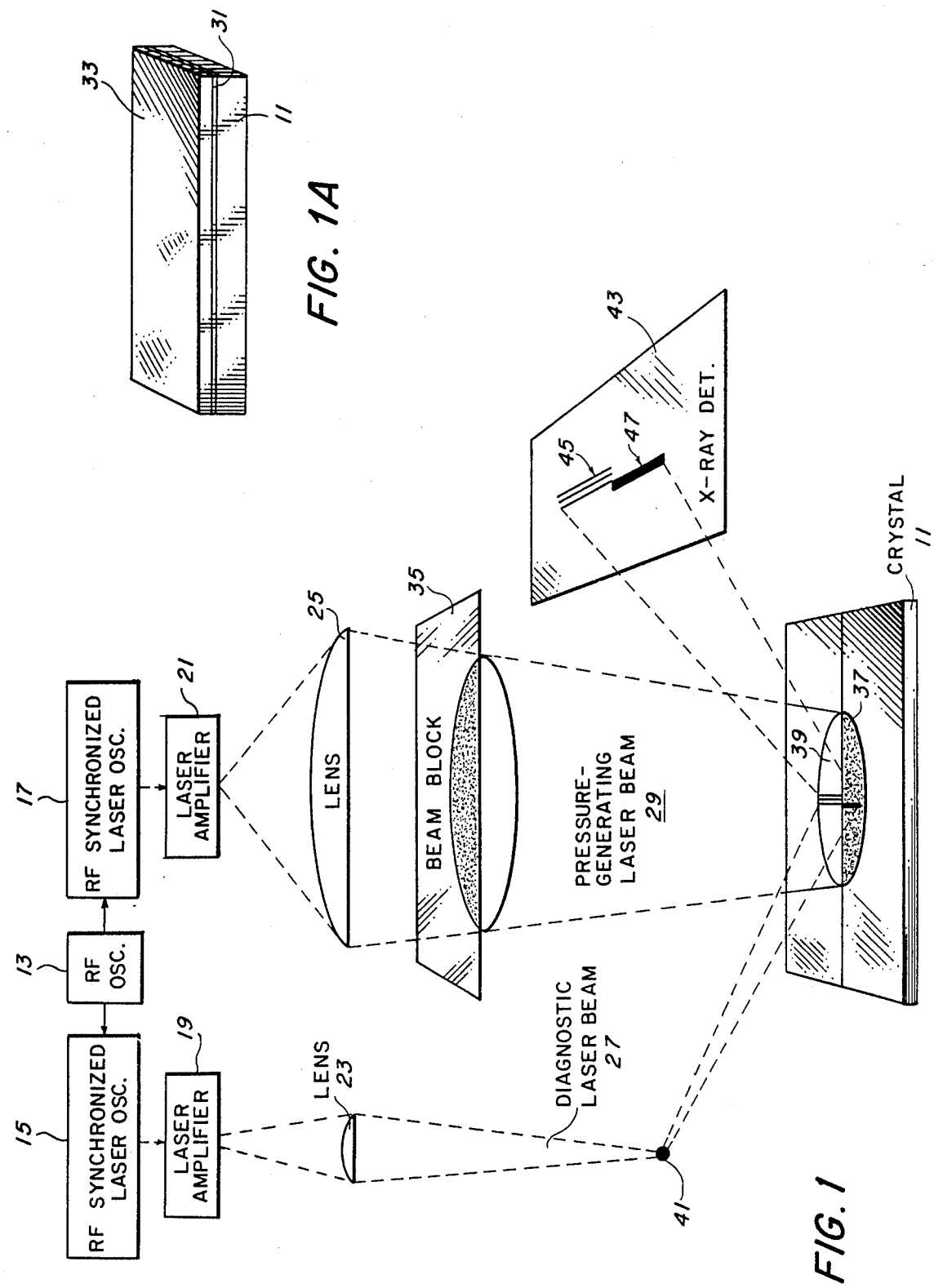

METHOD AND APPARATUS FOR TRANSIENT UNIT CELL MEASUREMENT

BACKGROUND OF THE INVENTION

The present invention relates to scientific instruments and particularly to a method and apparatus for measuring the lattice parameters of a single crystal material while that material is undergoing a transient shock wave.

The attainment of alternate materials phases at elevated static pressures has historically involved applied stresses in uniaxial, tetrahedral, or isotropic geometries. Transient high pressures have been applied to materials in the form of shocks. Shocks have resulted in changes in metallurgical properties, including phase changes, as determined by post-shock analysis.

A pressure field which is isotropic is called hydrostatic, since fluids (water) cannot support a shear stress and therefore support only isotropic pressure. However, this need not be so in crystalline solids, in which pressures can be directional. The details of nonhydrostatic pressures can be important to phase transitions, as in germanium, which transforms near 100 kbar with an applied uniaxial stress without a shear component, but at about 67 kbar in the presence of an additional shear component.

However, for solid-solid phase transitions, by whatever means of applying the elevated pressure, it has not been possible to directly determine the lattice parameters during the transition itself on any time scale below milliseconds. Also, the attainment of controlled strains in arbitrary directions has not heretofore been possible.

Lasers have been infrequently used in the past to thermally induce solid-solid phase changes in materials. In contrast, the body of work on laser-thermally-induced melting or annealing is very large. The effects of laser-induced shocks have been studied in certain aluminum alloys; metallurgical properties such as hardness and fatigue strength were found to be advantageously modified by laser-induced shocks. The mechanism for the production of shocks by lasers involves the ejection of mass from the surface of a material irradiated by the laser, which by conservation of momentum produces a pressure wave going into the volume of the material. Laser-produced shocks have been applied to solid materials in uniaxial geometries, although plasmas have also been shocked with cylindrical and spherical symmetry. Present laser systems built for a high degree of symmetry and uniformity of illumination are overpowered for the materials processing application, since they typically generate such high shock pressures that the temperature is raised sufficiently to induce melting and generate plasma.

OBJECT OF THE INVENTION

Accordingly, it is an object of the invention to provide a method and apparatus for examining the arrangement of atoms in a single crystal subjected to a transient stress.

Another object of the invention is to provide a method and apparatus for measuring the effects of laser-induced shocks on a single crystal.

Another object of the invention is to provide a method and apparatus which utilizes pulsed x-ray diffraction to measure the strain in a single crystal subjected to a transient compression.

Another object of the invention is to provide a method and apparatus for inducing phase transitions in a single crystal and measuring the lattice parameters of the phases on a time resolved basis.

Another object of the invention is to provide a method and apparatus for measuring the compression of a transiently shocked single crystal.

A further object of the invention is to provide a method and apparatus for examining a laser shocked region in a crystal lattice with pulsed x-ray diffraction.

SUMMARY OF THE INVENTION

These and other objects of this invention are achieved by providing a method and an apparatus which induces phase transitions in a single crystal and measures lattice parameters of the phases of a specially prepared sample on a time resolved basis. The apparatus includes a multiple beam laser which transmits one or more shock driver laser beams at a single crystal at controlled angles and irradiances and timings to produce single or multiple shock waves in the single crystal. One or more backlighter laser beams are also transmitted by the laser onto subsidiary targets located at predetermined positions and angles to produce x-rays which diffract from the crystal planes of the crystal undergoing the shock waves and are recorded by suitable detectors to provide a measurement of the lattice parameters of the crystal.

BRIEF DESCRIPTION OF THE DRAWINGS

These and other objects, features and advantages of the invention, as well as the invention itself, will become better understood by reference to the following detailed description when considered in connection with the accompanying drawings wherein like reference numerals designate identical or corresponding parts throughout the several views, and wherein:

FIG. 1 shows a first embodiment of the apparatus of the invention in operation;

FIG. 1A shows a sideview of a silicon crystal 11 coated first with aluminum and then with plastic.

DETAILED DESCRIPTION OF THE PREFERRED EMBODIMENTS

Figure 4:
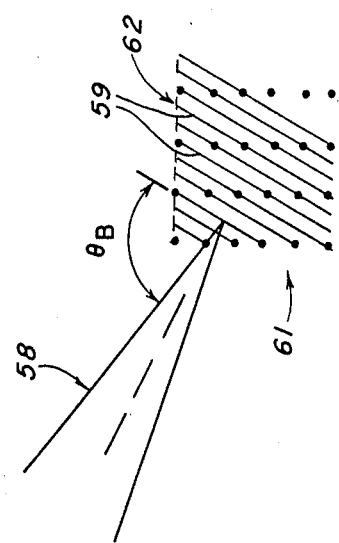
FIGS. 3 and 4 illustrate two different cases of Bragg diffraction.

Referring now to FIG. 1, a schematic block diagram of a first embodiment of the invention is shown. As will be explained, FIG. 1 illustrates an apparatus for the systematic and reproducible measurement of lattice compressions of a crystal 11 by shock waves, with temporal control sufficient to actually observe the propagation of a compression wave itself as it travels into the bulk of the material of the crystal 11. The crystal 11 itself may be any single crystal, which can be, for example, a 250 $\mu$m thick wafer that is 5 cm in diameter.

As shown in FIG. 1, a radio frequency (RF) oscillator 13 outputs a 50 megahertz (50 MHz) pulse to each of laser oscillators 15 and 17 to synchronize the laser beam outputs of laser oscillators 15 and 17 to a desired subharmonic of the 50 MHz output of RF oscillator 13. The laser beam outputs of oscillators 15 and 17 are respectively amplified by laser amplifiers 19 and 21 to produce associated amplified laser beam outputs, which are focused by respective lenses or focusing assemblies 23 and 25 to develop diagnostic and pressure-generating laser beams 27 and 29, respectively. The RF oscillator 13, laser oscillators 15 and 17, laser amplifiers 19 and 21, and lenses or focusing assemblies 23 and 25 are components well known in the optical art and, hence, require no further explanation.

The lens 25 focuses the pressure-generating laser beam 29 onto the crystal 11. The absorption properties of the crystal 11 for the wavelength of the laser beam 29 determines what is required to generate a pressure pulse at the focus of the pressure-generating laser beam 11. If each of the atoms in several atomic layers at the surface of the crystal 11 absorbs a sufficient amount of energy to vaporize or ionize, a pressure pulse will be produced which propagates into the crystal. The pressure pulse itself is produced by the gaseous expansion of the vaporized or ionized atoms.

On the other hand, if each atom in those atomic layers does not absorb a sufficient amount of energy to vaporize or ionize, the energy of the laser beam 29 is spread out over a larger volume of atoms and no vaporization or ionization of atoms occurs, no gaseous expansion takes place and no compression wave is launched.

So in the case where the crystal 11 is not very absorbing, the direct irradiation of the crystal 11 will result in a thermal response in the crystal 11 but not in the production of a pressure pulse. However, at very high irradiances it does not matter what material the crystal 11 is made of. At such high irradiances the intensity of the light of the laser beam 29 is sufficient in itself to produce ionization of the atoms in several atomic layers of the crystal 11. Once the ionization of atomic layers is produced, the laser beam 29 will interact with the plasma, or ions, and a different type of absorption will occur which produces a pressure pulse.

For purposes of this description, assume that: the pressure-generating laser beam 29 of FIG. 1 is an exemplary one nanosecond (1 nsec) pulse of 1.06 micron ($\mu$m) wavelength laser light at an irradiance varying from 0.8 to 8 joules per square centimeter (Jcm$^{-2}$); the diagnostic laser beam 27 is a 100 pico second (psec) pulse of 0.53 $\mu$m laser light having an irradiance of approximately 10 J cm$^{-2}$; and the 100 psec pulse of laser beam 27 is synchronous with but delayed slightly from the start of the 1 nsec pulse of laser beam 29. This laser beam 29 is focused by the lens 25 onto the target or target crystal 11 with an on-target beam diameter of 3.9 cm.

Further assume that the single crystal 11 is a silicon crystal and that it is desired to compress this silicon crystal 11. However, silicon itself does not have an abrupt absorption property. As a result, the silicon crystal 11 would absorb the energy of the 1.06 $\mu$m light in the laser beam 29 over an absorption length of several millimeters. Thus, the energy of the laser beam 29 would just heat the silicon crystal 11 and would be insufficient to vaporize or ionize atomic layers in the silicon crystal 11. Consequently, there would be no gaseous expansion in the crystal 11 and no compression wave generated in the silicon crystal 11.

Since the exemplary silicon crystal 11 does not have an abrupt absorption property, this problem can be solved by coating the silicon crystal 11 with a material which does have an abrupt absorption property. An aluminum coating or layer 31 (FIG. 1A) deposited on the silicon crystal 11 serves this function very well for the one micron (or 1.06 $\mu$m) wavelength laser beam 29. The aluminum layer 31 can be an exemplary 1000 angstroms in thickness and can be deposited on the top surface of the silicon crystal 11 by any suitable conventional semiconductor technique.

The aluminum layer 31 acts as an abrupt absorber to the incident radiation from the laser beam 29. This effectively prevents the penetration of the laser beam 29 into the silicon crystal 11 and, instead produces an aluminum plasma that in turn generates a pressure pulse for driving a moderate shock wave into the crystal lattice of the silicon crystal 11 to compress the crystal 11.

The compression produced in the lattice of the crystal 11 can be strengthened by confining the gaseous expansion of the aluminum plasma so that it cannot expand freely. This is accomplished by depositing a transparent plastic coating or layer 33 over the aluminum layer 31, as shown in FIG. 1A. This plastic layer 33 can have an exemplary thickness of 25 $\mu$m. Overcoating the aluminum layer 31 with the plastic layer 33 that is transparent to the 1.06 $\mu$m light of laser beam 29 causes the expanding aluminum plasma to be inertially confined between the silicon crystal 11 and the plastic layer 33, which in turn increases the strength of the shock or pressure pulse launched into the silicon crystal 11.

An optional beam block 35 is interposed between the lens 25 and the plastic-coated crystal 11 to pass only a first part of the pressure-generating laser beam 29 to a (shaded) first portion 37 of the crystal 11 and to block a second part of the laser beam 29 from impinging on a (clear) second portion 39 of the crystal 11. Thus, only the first portion 37 of the crystal 11 will be irradiated by the laser beam 29.

In order to view the behavior of the atoms in the crystal lattice of the silicon crystal 11 when the crystal 11 is subjected to the shock or pressure pulse produced by the laser beam 29, pulsed x-ray diffraction is used. X-ray diffraction, by Bragg's law, can measure the interplanar spacing between planes of atoms in the crystal lattice of the shocked crystal 11. The use of x-ray diffraction to view the crystal lattice of a shocked crystal 11 is explained below.

A small target 41, of solid, gaseous or even liquid material is placed at a selected location in space. For purposes of this discussion assume that the target 41 is a calcium-bearing target. After the shock or pressure pulse is launched in the first portion 37 of the silicon crystal 11 by the action of the laser beam 29, the diagnostic laser beam 27 (which contains approximately 10 J of 0.53 $\mu$m light in a 100 psec pulse) is tightly focused by the lens 23 to an approximate 40 $\mu$m diameter spot on the calcium-bearing target 41. This tightly focused laser beam 27 raises the temperature of the atoms in the target 41 to a very high temperature, causing ionized, helium-like calcium x-ray lines to be emitted in all directions. Of that emitted radiation, some of it is brought into the surface of the crystal 11 at the Bragg angle for the atomic planes of interest. The principles of Bragg x-ray diffraction are well known in the art and are explained in the book "Elements of X-Ray Diffraction" by B. D. Cullity, published by the Addison-Wesley Publishing Compay, Inc., Reading, Mass. in 1967.

The ionized helium-like calcium x-ray lines, produced by irradiating the target 41 with the high-power diagnostic laser beam 27, are Bragg-diffracted off the portions 37 and 39 of the silicon crystal 11 and recorded on a suitable x-ray detector 43 such as, for example DEF x-ray film manufactured by the Eastman Kodak Company, Rochester, N.Y. Other suitable x-ray detectors which could be used are an x-ray streak camera, an x-ray framing camera, an image intensifier and a charge coupled device which is sensitive to x-rays.

In the process of Bragg x-ray diffraction, the emitted x-rays incident to the uncompressed portion 39 of the silicon crystal 11 are diffracted off of the crystal 11 at a particular angle in space called the Bragg angle and recorded on the x-ray detector or x-ray film 43 as a spectrum 45. By changing the interplanar spacing in the portion 37 of the crystal 11, due to the compression caused by the pressure pulse, the Bragg angle is changed in that portion 37. Therefore, the x-rays in the compressed portion 37 of the silicon crystal 11 are diffracted off of the crystal 11 at a different Bragg angle and recorded on the x-ray detector 43 as a spectrum 47 which is different from the spectrum 45.

The x-ray detector 43 thus simultaneously shows, in the spectra 45 and 47, the recorded positions of the uncompressed and compressed portions 39 and 37, respectively, of the crystal 11. From these spectra 45 and 47, angular changes in the interplanar spacing between planes of atoms in the crystal lattice of crystal 11 can be readily determined by the spacing of known x-ray lines on the x-ray film 43 and by measuring the amount of deflection in the Bragg diffraction which is caused by the compression of the crystal 11.

It should be noted that the beam block 35, which was used in the above description to derive the spectra 45 and 47 is not an essential part of the apparatus of the invention. The positions of x-ray diffractions off of uncompressed and compressed portions of the crystal could be determined by means other than by using a beam block 35. For instance they could be determined by different geometric positions. It does not matter how the deflection in Bragg angle is measured. One alternate way of measuring the deflection in Bragg angle would be by first only generating the diagnostic laser beam 27 (without a compression of the crystal 11) to generate x-rays to record the positions of the uncompressed atomic layers. Next, the diagnostic laser beam 27 could be generated with the compression caused by the laser beam 29 to record the positions of the compressed atomic layers.

The laser beams 29 and 27 have to be closely synchronized in time with each other. This is due to the fact that shock waves travel at above $10^5$ centimeters per second and the physical width of the shock front is under $10^{-4}$ centimeters. Therefore, the time it takes a shock wave to travel its width is very short. As a consequence, good temporal control and good temporal resolution are required in the apparatus of the invention in order to properly study the response of the crystal lattice of crystal 11 to a compression wave propagating therein. The required control and resolution are achieved by synchronizing the laser beams 29 and 27 to each other, as discussed before.

Figure 2:
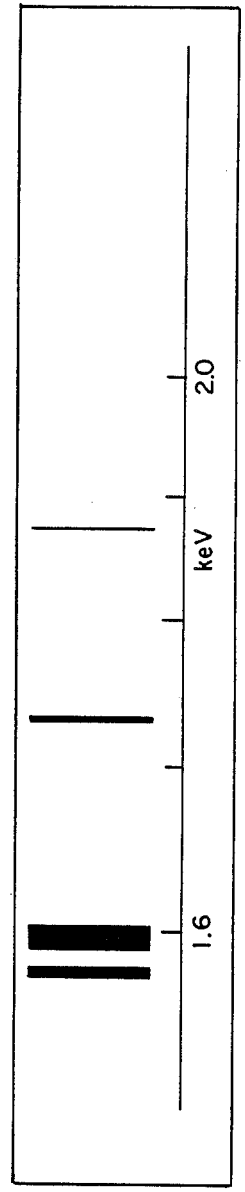
FIG. 2 is a representative example of an x-ray line spectrum produced by the pulsed x-ray diffraction from a laser-shocked single crystal.

FIG. 2 is a representative example of an aluminum spectrum of some of the x-ray lines that are produced by an aluminum target 41 and diffracted from a crystal (not silicon, in this example). This aluminum spectrum shows a few x-ray lines, with one very dark line and a few other lines spaced at different locations. It should be understood that if the target 41 were composed of a different material, then different x-ray wavelengths and a different spectrum would be derived as a function of the characteristic wavelengths of the constitutent atoms of that material in the target 41.

Figure 3:
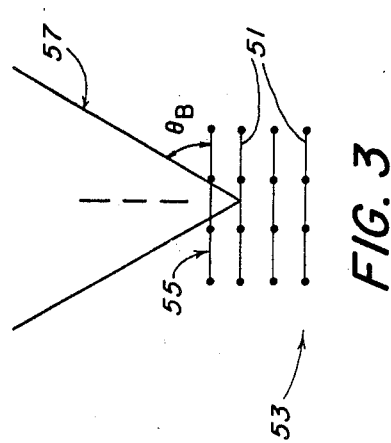

FIGS. 3 and 4 illustrate two different cases of Bragg-diffraction. FIG. 3 shows a symmetric Bragg-diffraction of an incident x-ray beam 57, wherein planes 51 of atoms of a crystal 53 are parallel to the surface 55 of the crystal 53. However, in all cases the Bragg angle $O_B$ is measured with respect to the planes 51 of atoms of the crystal 53, not necessarily with respect to the surface 55 of the crystal 53.

FIG. 4 shows an asymmetric Bragg diffraction of an incident x-ray beam 58, wherein planes 59 of atoms of a crystal 61 are at an angle to the surface 62 of the crystal 61. Once again, the Bragg angle $O_B$ is measured with respect to the planes 59 of atoms, not with respect to the surface 62 of the crystal 61.

By measuring symmetric and asymmetric planes of atoms of a crystal, the atomic arrangements of the crystal can be effectively measured in different directions to thereby reconstruct the three-dimensional arrangement of what is called the unit cell of the crystal lattice of the crystal. In this manner a new type of measurement can be performed, by which not just the interplanar spacing of the crystal lattice, but the unit cell size itself, can be determined as a function of transient compression conditions.

A compression pulse can be applied in any desired crystallographic direction of a crystal by cutting the surface of the crystal to be normal to the direction of propagation of the compression wave and then irradiating the crystal with laser beams as discussed before in relation to FIG. 1. The unit cell can then be measured under those conditions and the response of the unit cell can be determined for the case of a compression wave traveling in a preselected desired direction.

By utilizing such a technique in the embodiment of FIG. 1, an apparatus could be implemented which would have two or more x-ray sources probing in different directions and diffracting off of different atomic planes of a shocked single crystal in order to measure the atomic arrangements of that single crystal in different directions. Such an apparatus is shown in FIG. 5, which will now be discussed.

Figure 5:
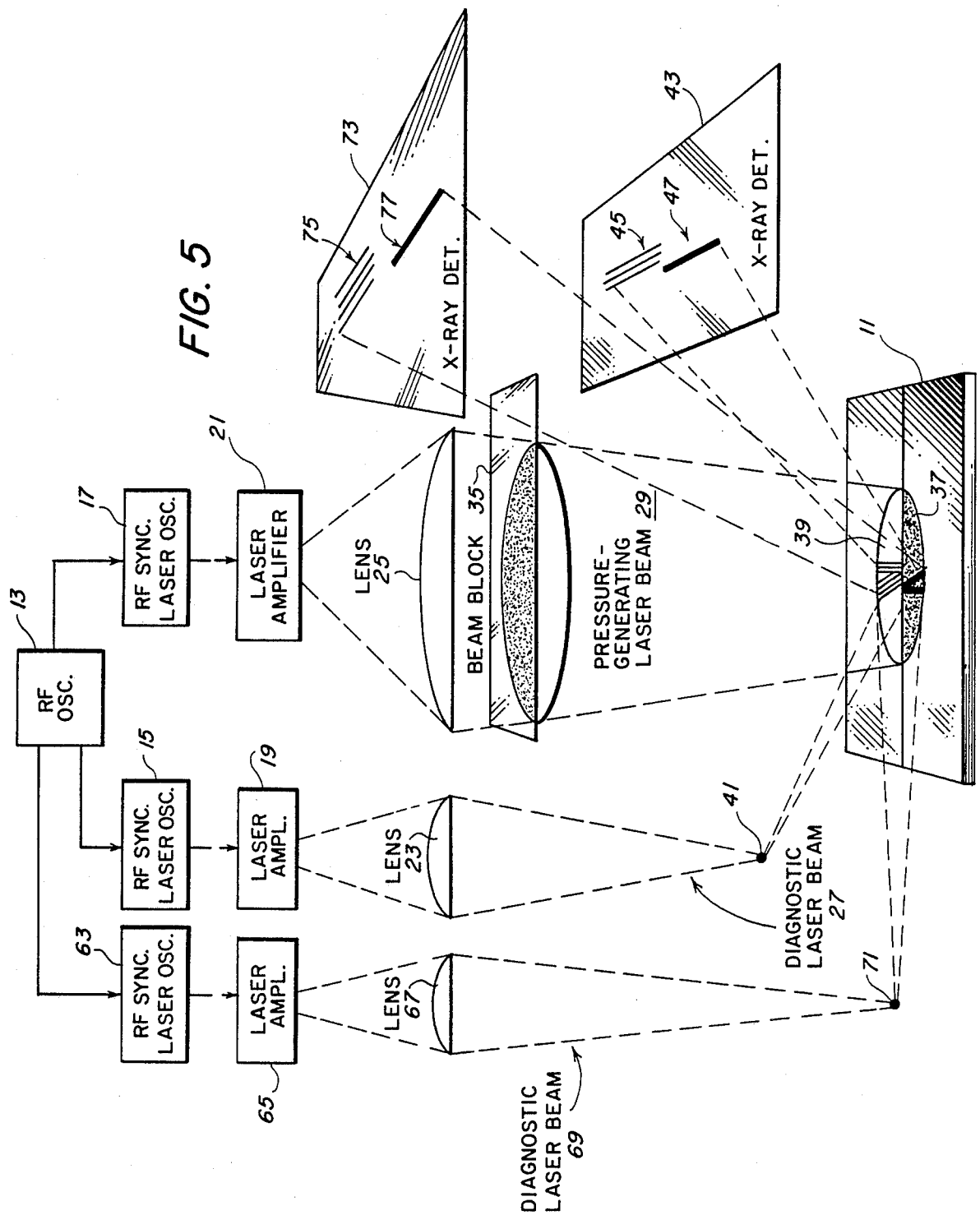
FIG. 5 shows a second embodiment of the apparatus of the invention in operation.

FIG. 5 shows a second embodiment of the apparatus of the invention. All of the structure shown in FIG. 1 is present in FIG. 5. In addition, an RF synchronized laser oscillator 63, laser amplifier 65, lens or focusing assembly 67, target 71, and x-ray detector 73 have been added to measure the atomic arrangements of the crystal 11 in another or second direction. The new elements 63, 65, 67, 71 and 73 are similar in structure and function to those of the elements 15, 19, 23, 41 and 43, respectively, and hence require no further description.

Like the laser oscillator 15, the laser oscillator 63 is synchronized by the RF oscillator 13 to develop a laser beam output shortly after the laser oscillator 17 has just started to develop a laser beam. The outputs of laser oscillators 63 and 15 are synchronously amplified by laser amplifiers 65 and 19, respectively, and then the outputs of amplifiers 65 and 19 are respectively tightly focused by their associated lenses 67 and 23 onto respective targets 71 and 41 to develop x-ray lines. The x-ray lines emitted from the targets 71 and 41 enter the surface of the crystal 11 at different angles from different orientations in space. As a result, the x-ray lines from the target 71 are Bragg-diffracted off of the portions 37 and 39 of the crystal 11 and recorded on the x-ray detector 73 as spectra 75 and 77, while the x-ray lines from the target 41 are Bragg-diffracted off of the portions 37 and 39 of the crystal 11 and recorded on the x-ray detector 43 as the spectra 45 and 47. Thus, the x-ray detector 73 simultaneously shows in the spectra 75 and 77 (derived from x-rays from target 71) the recorded positions of the uncompressed and compressed portions 39 and 37, respectively, of the crystal 11. At the same time, as discussed before, the x-ray detector 43 simultaneously shows in the spectra 45 and 47 (derived from x-rays emitted from target 41) the recorded positions of the uncompressed and compressed portions 39 and 37, respectively, of the crystal 11. The combination of the spectra recorded on the x-ray detectors 73 and 43 gives the response of the crystal lattice of crystal 11 in two of the three dimensions of three-dimensional space.

For certain crystal symmetries and certain orientations and surface cuts of the crystal 11, two targets (x-ray sources) and two x-ray detectors may suffice to indicate what the crystal 11 is doing in three dimensions when it is subjected to a pressure pulse from the pressure-generating laser beam 29. In other cases it may be necessary to have three targets (x-ray sources) and three x-ray detectors. Whether two or three of each are required to measure the unit cell is a matter which is easily determined by reference to the crystal symmetry and the orientation and cut of the crystal 11, according to principles well known in the art.

The temporal resolution of the x-ray diffraction probe into the crystal 11 can result from having a very short x-ray burst produced by the target (x-ray source) which in turn requires a short laser beam pulse focused onto the x-ray producing target. In that case the x-ray detector should be a temporally integrating detector, such as photographic film, charge coupled devices or an image intensifier. On the other hand, if a longer x-ray burst is produced by an x-ray producing target, the x-ray detector should be a temporally resolving detector, such as an x-ray streak camera or an x-ray framing camera.

Therefore, what has been described is an apparatus (and associated method) which utilizes pulsed x-ray diffraction to measure in one or more directions the lattice parameters in a single crystal subjected to a laser-induced compression pulse.

What is claimed and desired to be secured by Letters Patent of the United States is:

1. An apparatus for measuring the lattice parameters of a shocked single crystal, said apparatus comprising:
   a target located at a preselected position in space with respect to said crystal;
   means for transmitting a first laser beam pulse to said crystal to produce a transient shock wave in said crystal and for transmitting a second laser beam pulse to said target to cause said target to produce x-rays which are Bragg-diffracted from first atomic planes of said crystal as said crystal is undergoing the shock wave; and
   detection means for recording the Bragg-diffracted x-rays to provide a first measurement of the lattice parameters of said crystal during compression by said shock wave.

2. The apparatus of claim 1 further including:
   means interposed between said transmitting means and said crystal for allowing a first part of the first laser beam pulse to produce a transient shock wave in a first portion of said crystal and for preventing a second part of the first laser beam pulse from producing a transient shock wave in a second portion of said crystal;
   said detection means being responsive to x-rays that are Bragg-diffracted off of the first and second portions of said crystal for simultaneously recording the spacings of atomic planes in the first and second portions of said 3. The apparatus of claim 1 wherein said transmitting means comprises:
   first and second laser oscillators for respectively developing first and second laser output pulses;
   RF means for developing an output to synchronize the first and second laser output pulses to each other;
   first and second amplifier means for respectively amplifying the first and second laser output pulses;
   means for focusing said amplified first laser output pulse to develop said first laser beam pulse; and
   means for focusing said amplified second laser output pulse to develop said second laser beam pulse.

4. The apparatus for claim 3 further including:
   means interposed between said transmitting means and said crystal for allowing a first part of the first laser beam pulse to produce a transient shock wave in a first portion of said crystal and for preventing a second part of the first laser beam pulse from producing a transient shock wave in a second portion of said crystal;
   said detection means being responsive to x-rays that are Bragg-diffracted off of the first and second portions of said crystal for simultaneously recording the spacings of atomic planes in the first and second portions of said crystal.

5. The apparatus of claim 4 wherein said single crystal does not have an abrupt absorption property and said apparatus further includes:
   a first coating of a material having an abrupt absorption property and being deposited on said crystal; and
   a transparent layer of material disposed on said first coating to confine a gaseous expansion between said transparent layer and said crystal, said expansion producing said transient shock wave.

6. The appartus of claim 1 wherein said single crystal has an abrupt absorption property.

7. The apparatus of claim 1 wherein said single crystal does not have an abrupt absorption property and said apparatus further includes:
   a first coating of a material having an abrupt absorption property and being deposited on said crystal; and
   a transparent layer of material disposed on said first coating to confine a gaseous expansion between said transparent layer and said crystal, said expansion producing said transient shock wave.

8. The apparatus of claim 7 wherein:
   said single crystal is silicon;
   said first coating is metallic; and
   said transparent layer is plastic.

9. The apparatus of claim 8 wherein:
   said first coating is aluminum.

10. The apparatus of claim 1 wherein said transmitting means further transmits a third laser beam pulse synchronized to said first and second laser beam pulses, said apparatus further including:
    a second target located at a second preselected position in space with respect to said crystal and being responsive to said third laser beam pulse for providing x-rays which are Bragg-diffracted from second atomic planes of said crystal as said crystal is undergoing the shock wave; and second detection means for recording the x-rays which are Bragg-diffracted from said second atomic planes to provide a second measurement of the lattice parameters of said crystal synchronous with the first measurement.

11. The apparatus of claim 10 further including:

means interposed between said transmitting means and said crystal for allowing a first part of the first laser beam pulse to produce a transient shock wave in a first portion of said crystal and for preventing a second part of of the first laser beam pulse from producing a transient shock wave in a second portion of said crystal;

said detection means being responsive to x-rays from said target that are Bragg-diffracted off of the first and second portions of said crystal for simultaneously recording the spacings of atomic planes in the first and second portions of said crystal in a first direction, and said second detection means being responsive to x-rays from said second target that are Bragg-diffracted off of the first and second portions of said crystal for simultaneously recording the spacings of atomic planes in the first and second portions of said crystal in a second direction.

12. The apparatus of claim 10 wherein said transmitting means comprises:

first, second and third laser oscillators for respectively developing first, second and third laser output pulses;

RF means for developing an output to synchronize the first, second and third laser output pulses to each other;

first, second and third amplifier means for respectively amplifying the first, second and third laser output pulses;

means for focusing said amplified first laser output pulse to develop said first laser beam pulse;

means for focusing said amplified second laser output pulse to develop said second laser beam pulse; and means for focusing said amplified third laser output pulse to develop said third laser beam pulse.

13. The apparatus of claim 12 further including:

means interposed between said transmitting means and said crystal for allowing a first part of the first laser beam pulse to produce a transient shock wave in a first portion of said crystal and for preventing a second part of the first laser beam pulse from producing a transient shock wave in a second portion of said crystal;

said detection means being responsive to x-rays from said target that are Bragg-diffracted off of the first and second portions of said crystal for simultaneously recording the spacings of atomic planes in the first and second portions of said crystal in a first direction, and said second detection means being responsive to x-rays from said second target that are Bragg-diffracted off of the first and second portions of said crystal for simultaneously recording the spacings of atomic planes in the first and second portions of said crystal in a second direction.

14. The apparatus of claim 13 wherein said single crystal does not have an abrupt absorption property and said apparatus further includes:

a first coating of a material having an abrupt absorption property and being deposited on said crystal; and a transparent layer of material disposed on said first coating to pass said first laser beam pulse and confine a gaseous expansion between said transparent layer and said crystal, said expansion producing said transient shock wave.

15. A method for measuring the lattice parameters of a single crystal, said method comprising the steps of:

locating a target at a preselected position in space with respect to said crystal;

transmitting a first laser beam pulse to the crystal to produce a transient shock wave in the crystal;

transmitting a second laser beam pulse to the target to cause the target to produce a set of x-rays which are Bragg-diffracted from first atomic planes of the crystal as the crystal is undergoing the transient shock wave; and recording the set of Bragg-diffracted x-rays to provide a first measurement of the lattice parameters of the crystal.

16. The method of claim 15 further including the steps of:

transmitting a third laser beam pulse at the target to cause the target to produce a second set of x-rays which are Bragg-diffracted from associated unshocked atomic planes of the crystal; and recording the second set of Bragg-diffracted x-rays to provide a second portion of the first measurement.

17. The method of claim 15 further including after said transmitting a first laser beam pulse step the step of:

preventing part of the first laser beam pulse from being transmitted to the crystal so that the recorded first measurement is comprised of the spacings of atomic planes in shocked and unshocked portions of the crystal.

18. The method of claim 15 further including the steps of:

locating a second target at a second preselected position in space with respect to the crystal;

transmitting synchronously with the second laser beam pulse a third laser beam pulse at the second target to cause the second target to produce x-rays which are Bragg-diffracted from second atomic planes of the crystal as the crystal is undergoing the transient shock wave; and recording the Bragg-diffracted x-rays from the second atomic planes of the crystal to provide a second measurement of the lattice parameters of the crystal.

19. The method of claim 18 further including after said transmitting a first laser beam pulse step the step of:

preventing part of the first laser beam pulse from being transmitted to the crystal so that each of the recorded first and second measurements is comprised of the spacings of associated atomic planes in shocked and unshocked portions of the crystal.

20. A method for measuring the lattice parameters of a single crystal, said method comprising the steps of:

locating a first target at a first preselected position in space with respect to the crystal;

locating a second target at a second preselected position in space with respect to the crystal;

respectively transmitting first and second laser beam pulses at the first and second targets to cause the first and second targets to produce first and second sets of x-rays which are respectively Bragg-diffracted from associated first and second sets of unshocked atomic planes of the crystal;

transmitting a third laser beam pulse at the crystal to produce a transient shock wave in the crystal;

respectively transmitting fourth and fifth laser beam pulses at the first and second targets to cause the first and second targets to produce third and fourth sets of x-rays which are respectively Bragg-diffracted from associated first and second sets of shocked atomic planes of the crystal; and selectively recording the first and second sets of x-rays as a first measurement of the lattice parameters of the crystal and the second and fourth sets of x-rays as a second measurement of the lattice parameters of the crystal.

* * * * *